(12) United States Patent
Manalis et al.

(10) Patent No.: US 8,722,419 B2
(45) Date of Patent: *May 13, 2014

(54) FLOW CYTOMETRY METHODS AND IMMUNODIAGNOSTICS WITH MASS SENSITIVE READOUT

(75) Inventors: Scott R. Manalis, Cambridge, MA (US); Thomas P. Burg, Goettingen (DE); Michel Godin, Beaconsville (CA); Kenneth Babcock, Santa Barbara, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 836 days.

This patent is subject to a terminal disclaimer.

(21) Appl. No.: 12/305,733

(22) PCT Filed: Jun. 15, 2007

(86) PCT No.: PCT/US2007/071309
§ 371 (c)(1),
(2), (4) Date: May 12, 2010

(87) PCT Pub. No.: WO2008/060713
PCT Pub. Date: May 22, 2008

(65) Prior Publication Data
US 2010/0227310 A1    Sep. 9, 2010

Related U.S. Application Data

(60) Provisional application No. 60/816,274, filed on Jun. 22, 2006, provisional application No. 60/833,456, filed on Jul. 26, 2006, provisional application No. 60/846,013, filed on Sep. 20, 2006.

(51) Int. Cl.
*G01N 24/00* (2006.01)
*G01N 33/543* (2006.01)
*G01N 35/08* (2006.01)
*G01N 31/00* (2006.01)

(52) U.S. Cl.
USPC ............. 436/173; 435/286.5; 435/287.1; 436/518; 436/523; 436/10; 436/52; 73/32

(58) Field of Classification Search
USPC ............. 435/7.1, 7.2, 287.2, 287.8, 286.5, 435/287.1; 436/517, 518, 523, 524, 528, 436/10, 173, 52; 422/502; 73/592, 32
See application file for complete search history.

(56) References Cited

U.S. PATENT DOCUMENTS 8,087,284 B2 * 1/2012 Babcock et al. ............. 73/32 A

OTHER PUBLICATIONS

Burg et al. Suspended microchannel resonators for biomolecular detection, Applied Physics Letters 83 (13): 2698-2701 (Sep. 29, 2003).*

* cited by examiner

*Primary Examiner* — Gail R Gabel
(74) *Attorney, Agent, or Firm* — Mark Rodgers

(57) ABSTRACT

Mass cytometry method. In one aspect, the method includes providing a sample having at least one cell type and mixing the sample with material such as nanoparticles functionalized with affinity molecules for the at least one cell type. The sample is transported through a suspended microchannel resonator to record a mass histogram and a cell count for the at least one cell type is determined from the histogram.

2 Claims, 4 Drawing Sheets

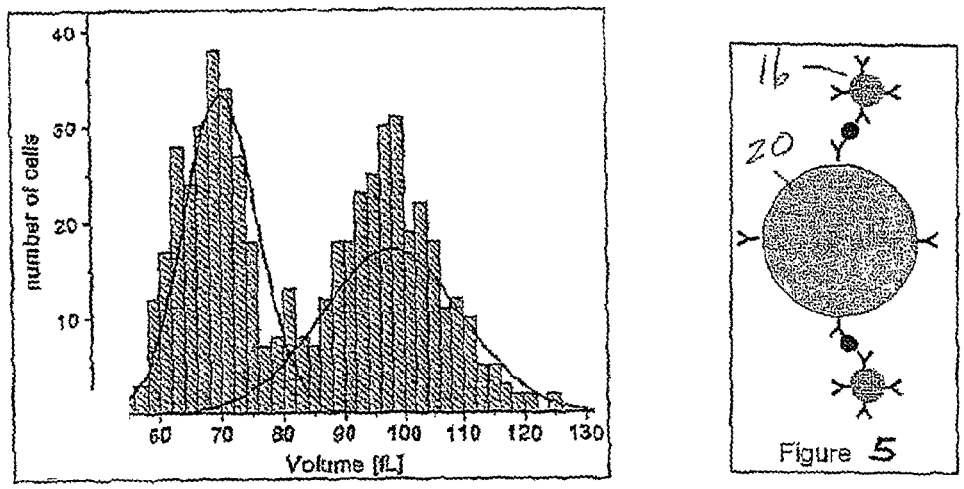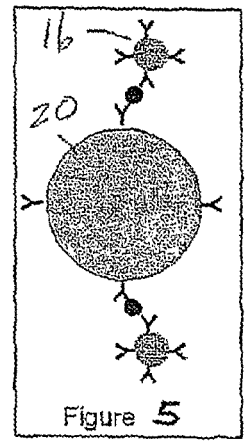
Figure 4
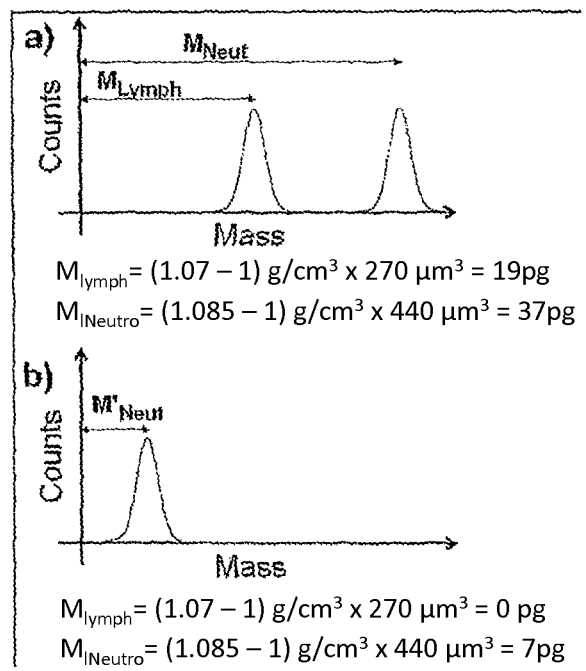
$M_{lymph} = (1.07 - 1)$ g/cm³ × 270 μm³ = 19pg
$M_{lNeutro} = (1.085 - 1)$ g/cm³ × 440 μm³ = 37pg
$M_{lymph} = (1.07 - 1)$ g/cm³ × 270 μm³ = 0 pg
$M_{lNeutro} = (1.085 - 1)$ g/cm³ × 440 μm³ = 7pg
Figure 6

● target
● background
Option 3: Assay without surface
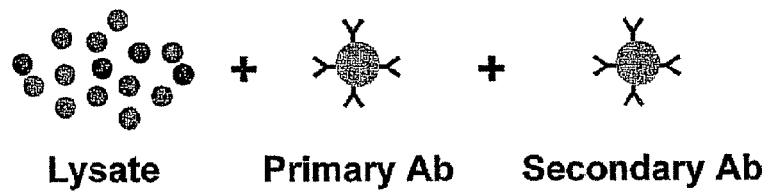
Lysate     Primary Ab     Secondary Ab
Histogram
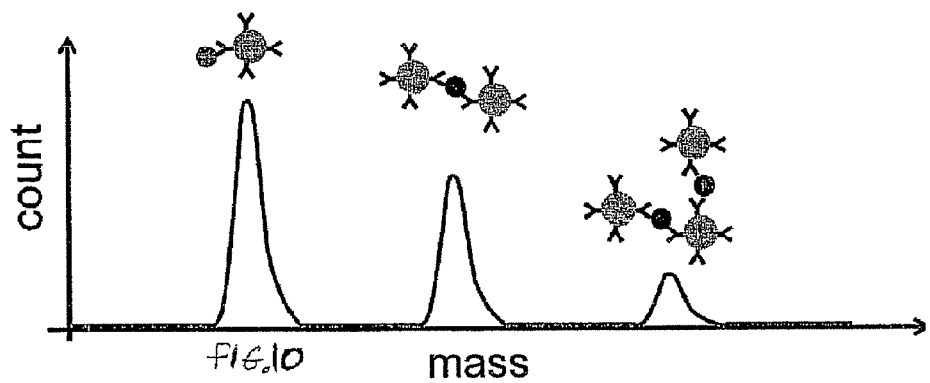
FIG. 10    mass

FLOW CYTOMETRY METHODS AND IMMUNODIAGNOSTICS WITH MASS SENSITIVE READOUT

This Application is a U.S. national phase application under 35 U.S.C. §371 of international PCT application no. PCT/US2007/071309, filed Jun. 15, 2007, which claims priority to provisional application Ser. No. 60/816,274 filed Jun. 22, 2006; provisional application Ser. No. 60/833,456 filed Jul. 26, 2006; and provisional application Ser. No. 60/846,013 filed Sep. 20, 2006. Each of the above-cited patent applications is incorporated herein by reference in their entirety.

BACKGROUND OF THE INVENTION

This invention relates to flow cytometry and more particularly to flow cytometry methods utilizing a mass sensor.

Flow cytometers (FCM) for enumerating the absolute levels of cells and their subsets are used extensively for blood and other clinical samples and show promise for identifying pathogenic bacteria. Flow cytometry is a mature technology that uses hydrodynamics to focus a stream of aligned and single-file particles, optics to illuminate a particle with lasers or other light sources, and detectors to resolve scattered light as well as, in some embodiments, fluorescent signals. Specificity to a target subset of cells is achieved by attaching fluorescent labels to the subset with affinity molecules such as antibodies. For many applications, the FCM functions as a highly automated fluorescent microscope. Typical FCM's cost in the range of $40,000 to $150,000. Even the most compact and economical FCM on the market today is still considered a bench top instrument and costs approximately twenty thousand dollars. A significant portion of the cost to build FCMs is directed toward the optical readout.

Another class of flow cytometers is the Coulter Counter (CC). By measuring electrical impedance through an aperture, the Coulter Counter can measure cell count and volume. Coulter Counters are used routinely as hematological analyzers for red and white blood cells. Other applications include cell biology, food analysis, cosmetics, metals, marine biology, etc.

A major clinical application for flow cytometry is staging HIV-infected patients by counting CD4+ T lymphocytes. This counting provides information about how far patients have progressed along the HTV disease course and is crucial for determining when to start or change antiretroviral therapy. Recently, two relatively cheaper, simpler and more robust CD4+ cell counting approaches have been evaluated. One approach is known as Cytospheres (Beckman Coulter), in which monoclonal antibody-coated latex spheres bind to cell expressing CD4 surface antigen. In another known approach, an automated two parameter FCM (CyFlow from Partec) is used in a volumetric protocol to count CD4+ cells that are marked with a single monoclonal fluorochrome-conjugated antibody in a known volume of blood. An erythrocyte lysing procedure is not required.

SUMMARY OF THE INVENTION

In one aspect, the mass cytometry method of the invention includes providing a sample having at least one cell type and mixing the sample with material functionalized with affinity molecules for the at least one cell type. The sample is transported through a suspended microchannel resonator, and the resonant frequency is monitored and a mass histogram is recorded. A cell count for the at least one cell type is determined from the histogram.

The material for enhancing the mass of the at least one cell type includes nanoparticles, microparticles, polymer or virus or any substance that can be selectively attached to cells. Nanoparticles are particularly preferred. In a preferred embodiment, the sample includes multiple cell types and the histogram includes components representing cells, cells with attached nanoparticles and the nanoparticles themselves. Preferred nanoparticles are gold and have a diameter of approximately 100 nm and a mass of approximately 10 fg.

In another aspect, the mass cytometry method of the invention includes disposing a sample containing cells in a surrounding solution whose mass density is selected to match substantially the mass density of cells in the sample to make the cells neutrally buoyant. In this way, fewer nanoparticles are necessary to attach to the cells than would otherwise be the case in order to create a distinct mass signal for the target subset of cells.

In yet another aspect of the invention the mass cytometry method includes providing a sample having at least one cell type and functionalizing a channel wall of a suspended microchannel resonator to capture the at least one cell type. The sample is transported through the resonator and discrete steps in resonant frequency are observed as cells attach to the channel wall. In a preferred embodiment of this aspect of the invention nanoparticle-labeled affinity molecules are subsequently transported through the resonator so as to increase specificity and the resulting resonant frequency is monitored.

In yet another aspect, the invention is an immunodiagnostic method including functionalizing micron-sized carrier beads that may be magnetic with an antibody receptor and exposing the beads to a sample containing a specific antigen. The beads are collected and rinsed and exposed to secondary antibodies labeled with nanoparticles. The mixture is then transported through a suspended microchannel resonator and a target concentration is determined from a mass histogram. In a preferred embodiment of this aspect of the invention multiple species are detected and measured using nanoparticles of different masses that are functionalized for specific attachment to selected targets.

In yet another aspect, the invention is a mass cytometry method comprising mixing nanoparticles conjugated to primary and secondary antibodies with targets that have multiple binding epitopes to form a sample including dimers having two connected nanoparticles. The sample is flowed through a suspended microchannel resonator to measure the mass of each component in the sample and to create a histogram. The dimers are counted in relation to initial target concentration.

The methods of the invention maybe applied to the counting of CD4+ cells, microbial populations such as bacteria or spores, and viruses.

The suspended microchannel resonator utilized in this invention, which does not require optics, can be packaged compactly (potentially handheld) for point-of-use applications and is extremely robust. An SMR sensor is disposable and costs $10-100 per chip and the reader might ultimately cost in the range of $100-1,000. A single chip can be used for many assays before needing to be replaced.

By using mass readout, such as with a suspended microchannel resonator, the inventors estimate that the primary cost per assay would be determined by the reagents. We further envision that a low-cost and handheld FCM would enable new applications that are not accessible to today's expensive and benchtop systems. Whereas FCMs that rely on optics can detect up to $10^5$ cells per second, the throughput of a single SMR sensor is expected to be in the range of 1-10 cells per second. However, the throughput of an integrated mass readout can be increased by transporting the sample through an array of resonators in parallel. Since each resonator does not need individual fluidic addressing, it should be possible to operate 100-1,000 resonators on a single chip.

The suspended microchannel resonator that relies on mass readout provides an extraordinarily high dynamic range since the parameter being measured is frequency. For instance, detecting the addition of a 100 nm nanopartical on 10 μm cell requires that a $1:10^6$ change in signal be resolved. This resolution is straightforward to achieve with a mass readout but is difficult to achieve with an electrical readout as in the Coulter Counter.

We note that mass-based measurements as disclosed herein can be used also for cell studies other than assay-based detection. For example, a growing body of research seeks to assess the effects of drugs, physiological entities, and environmental factors on cellular function. Mass measurements can elucidate these effects by comparing masses of individual cells or colonies with and without drugs being present, for example.

BRIEF DESCRIPTION OF THE DRAWING

FIG. 4 is a histogram showing number of cells versus volume for red blood cells in two different states.

FIG. 5 is a schematic illustration showing micron-sized magnetic carrier beads functionalized with an antibody receptor.

FIGS. 6*a* and 6*b* are graphs of cell counts vs. mass.

FIG. 10 is a schematic illustration and histogram of another embodiment of the invention.

DESCRIPTION OF THE PREFERRED EMBODIMENT

Micro- and nanomechanical resonators enable the direct measurement of mass on the molecular scale through observation of shifts in resonant frequency. Sub-micron thick resonators operating in high vacuum are capable of resolving masses of a few zeptogram, and similar devices have been used to detect single virus particles and the adsorption of molecular monolayers in air. The prospect of achieving such sensitivity together with the high scalability and low cost manufacturing associated with semiconductor processing has stimulated great interest in applying resonant mass detection to chemical and biological applications. Heretofore, however, only resonant transducers operated in air or vacuum have been able to provide sufficient resolution for such applications. The inventors herein have recently shown that fluid filled microfabricated resonators remove this limitation and can measure a mass of less than a femtogram in an aqueous environment. A significant aspect to achieving such mass resolution is the observation that the quality factor of a thin hollow microcantilever can be as high as 15,000 for dry and for water filled devices. The resulting sub-femtogram resolution has enabled single cells and nanoparticles as small as 100 nm to be weighed with high precision as they flow through the resonating microchannel.

Using conventional silicon micromachining and wafer-scale vacuum packaging, 3 by 8 μm (height×width) suspended microchannels in the shape of 200 μm long and 33 μm wide microcantilevers have been designed at the Massachusetts Institute of Technology and fabricated at a foundry. Microfluidic bypasses of low flow resistance connect an inlet and an outlet of the suspended microchannel to macroscopic tubing. This arrangement enables the rapid exchange of microliter sample volumes without having to drive a large fluid volume through the thin cantilever. Since the flow rate through the suspended microchannel is typically approximately 100 pL/sec when weighing particles, it is possible to perform assays with extremely small amounts of reagents.

A suspended microchannel resonator employed in the present invention utilizes a fluidic microchannel embedded in a resonating cantilever. Other configurations may also be used, such as a microfluidic channel suspended at each end so that the center portion may resonate. The mechanical resonant frequency of the sensor changes in relation to the mass of a cell or other target passing through the microchannel, and this change can be measured with high precision. An illustration of a suspended microchannel resonator is shown in the inset in FIG. 2*a*.

Figure 1:
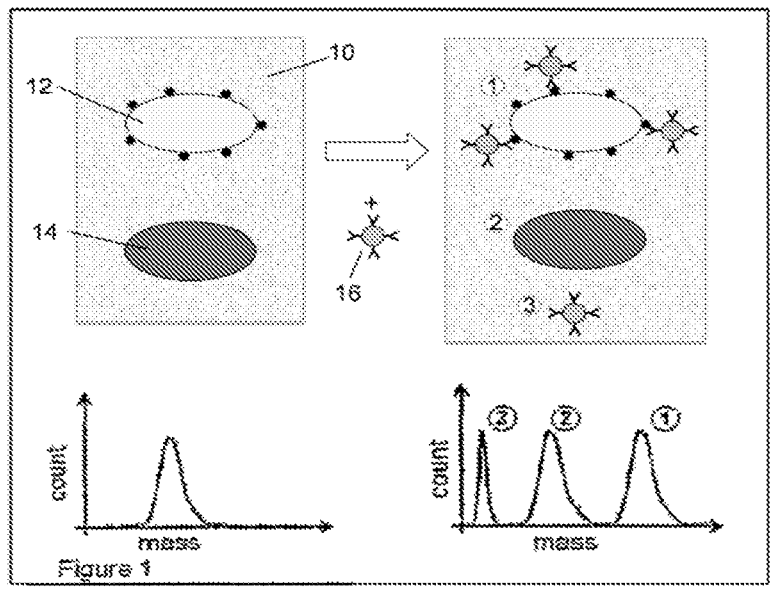
FIG. 1 is a schematic illustration of one embodiment of the invention disclosed herein.

A first embodiment of the invention will now be described in conjunction with FIG. 1. A sample 10 includes two cell types 12 and 14 that are mixed with nanoparticles (NP) 16 functionalized with affinity molecules for one of the cell types. The mixing creates cells 12 with attached nanoparticles 16, cells 14 alone and some nanoparticles 16 alone. It is noted that the use of nanoparticles is exemplary; other substances such as microparticles, viruses or polymer may be used to enhance the mass of the cells. The sample is then transported through a suspended microchannel resonator and a mass histogram is recorded. As shown in the figure, the histogram will consist of three components: cells, cells with NPs, and NPs. In order to identify the cell only component, a reference histogram is recorded from the unprocessed sample. If the mass distribution for unlabeled cells is sufficiently narrow, the histogram from the NP-labeled cells will be distinct from the cell histogram. Thus, it is possible to obtain a total cell count and a subset cell count.

Figure 2:
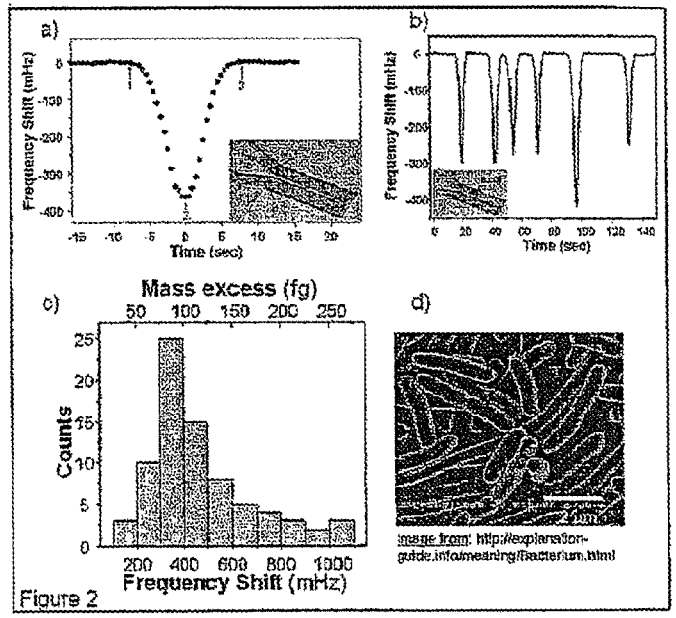
FIG. 2*a* is a graph of frequency shift versus time.
FIG. 2*b* is a graph of frequency shift versus time.
FIG. 2*c* is a histogram showing counts versus frequency shift.
FIG. 2*d* is an electron micrograph of various sized *E. coli*.
Figure 3:
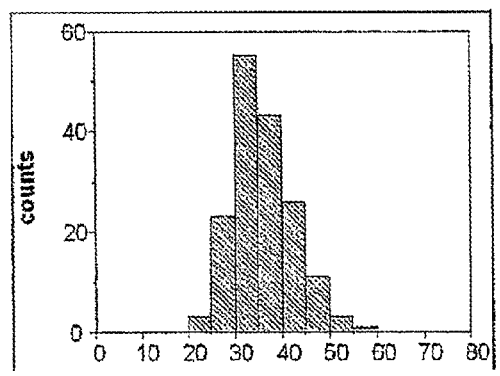
FIG. 3 is a histogram of counts versus frequency shift for 100 nm gold nanoparticles.

The inventors' lab has performed experiments that provide a partial validation of this approach. With reference to FIG. 2, FIGS. 2*a* and 2*b* show a mass response from *E. coli* as it is transported through a suspended microchannel resonator and FIG. 2*c* shows the resulting histogram. FIG. 2*d* is an electron micrograph of various sized *E. coli*. The average *E. coli* mass is 100 fg and the distribution ranges from approximately 50-250 fg. A histogram obtained from 100 nm gold nanoparticles is shown in FIG. 3. Each nanoparticle has a mass of approximately 10 fg. A 150 nm gold nanoparticle would be expected to have a mass of 30 fg. Thus, if these nanoparticles were functionalized for a particular species of *E. coli*, a distinct peak in the histogram would appear provided that approximately 5 nanoparticles or more are attached to each *E. coli*. Fewer nanoparticles will be required if the intrinsic cell mass distribution becomes narrower. Such a narrow cell mass distribution is the case for many types of mammalian cells. For example, FIG. 4 shows the volume distribution of red blood cells in two different states and the peak width is about 30% of the average volume. In this example, we assume that the volume distribution of red blood cells would correlate to their mass distribution. While the mass distribution of *E. coli* shown in FIG. 2 is quite large with respect to the average mass, it may nonetheless be possible to distinguish bacterial species, or other species of biological entities, with good confidence via mass alone. For example, in a complex mixture containing *B. anthracis* spores, the spores and their mass distributions may be sufficiently distinct in the suspended microchannel resonator readout from other entities that they can be detected with no nanoparticle mass labels at all.

In another preferred embodiment of the invention channel walls of the suspended microchannel resonator are functionalized to capture a specific cell type. A sample is transported through the resonator and if the cell type is present, discrete steps in the frequency response will be observed as the cells attach to the wall surface. All other cells will pass through the resonator and will result in a transient change in frequency. This approach has been previously proposed for fluorescent optical readout, but to the inventors' knowledge not for mass readout. To increase specificity, nanoparticle-labeled affinity molecules can subsequently be transported through the resonator and the resulting frequency response can be monitored. In this case, a similar idea has been previously proposed in which the optical transmission of a channel is measured as the nanoparticles bind to the cell surface and reduce transparency.

It is important to note that for all of these approaches set forth above, there are many types of microfabricated densitometers that are suitable. The suspended microchannel resonator is one example. Other embodiments, however, have been published previously. It is to be understood that whenever a suspended microchannel resonator is referred to herein, other densitometers are included.

Mass-based studies can also measure changes in individual cells or of colonies as the cells undergo mitosis or other processes. Such studies can be done either in a flow-based setup via successive measurements, or by capturing or fixing cells to the sensor walls and monitoring their mass changes in real time. Such a protocol will be useful for studies of drug efficacy and drug resistance on mitosis, colony growth, and other physiological effects on cells.

In addition to counting cells, mass-based detection can also be used to measure biomolecular concentration and interactions, and perform immunodiagnostic assays. For example, a common immunodiagnostic method utilizes bead-based assays in which targets are selectively bound to micron-scale beads coated with affinity ligands or antibodies. This method is similar to performing an ELISA assay on beads. By using an optical label, or fluorophor, binding may be detected optically. See, for example, commercial assays and optical readers currently sold by Luminex. By using fluorescent markers at various emission frequencies, such an assay can be highly multiplexed. Variants of this approach include magnetic and electrochemiluminescent readout (Bioveris). In addition to diagnostics, these approaches are also used in measurement of kinase activities in cell-signaling and cellular pathway studies, drug screening and kinase inhibitor characterization (Qiagen). We envision that similar assays can be accomplished by replacing optical readout with a mass sensor.

As shown in FIG. 5, micron-sized magnetic carrier beads 20 are functionalized with an antibody receptor and exposed to a sample containing a specific antigen. The beads are collected, rinsed and exposed to secondary antibodies that are labeled with 10-100 nm sized gold nanoparticles 16.

The mixture is then transported through the suspended microchannel resonator and the target concentration is determined by a mass histogram. The advantage of replacing optics with the mass sensor is primarily cost. In addition to cost, cytometry with mass readout is far more robust and easier to miniaturize without degrading performance. However, it is possible that the sensitivity can be improved for certain types of assays, since the addition of a single nanoparticle on a carrier bead can in principle be detected. In addition, it may be possible to achieve a degree of multiplexing, that is, the simultaneous detection and measurement of multiple species, by using nanoparticles of different masses that are functionalized for specific attachment to various targets. For example, an assay could be designed such that heavier, 100 nm particles, could be selectively bound to a target A, while lighter, 20 nm particles, are selectively bound to a target B. The concentration of the targets A and B will be reflected by distinct peaks in the sensor histogram, much as shown earlier in FIG. 1.

This approach can be extended to many bead-based and related assay protocols that are currently in the art, including any that result in selective binding of bio-molecules, labels, or any other entity that results in a change in mass. Conversely, useful protocols can include enzymatic or other reactions that cleave bonds and release NPs, labels or other entities, so as to produce a detectable reduction in mass of a cell, bead, or other target.

There are many applications for the cell counting methods disclosed herein. For example, a major clinical application for flow cytometry is staging HIV-infected patients by counting CD4+ T lymphocytes. This counting provides information about how far the patients have progressed along the HIV disease path and is crucial for determining when to start or change antiretroviral therapy. It is generally accepted that the most suitable laboratory diagnosis occurs when the CD4+ T-cell count falls below 200/µl of blood or 14% of total lymphocytes. See, Brando et al., "Cytofluorometric methods for assessing absolute numbers of cell subsets in blood," *Cytometry*, 42 327 (2000).

The general approach according to this invention for counting specific cells has been discussed above in conjunction with FIG. 1. The sample is mixed with gold nanoparticles (NP) functionalized with antibodies for the target cell type. The sample is then transported through the resonator and a mass histogram is recorded. For this concept to work properly it is necessary to bind enough nanoparticles to the cell surface such that the target cells are sufficiently heavier than the intrinsic mass variation of the cell population. For example, lymphocytes such as CD4+ T lymphocytes weigh approximately 20 pg in water and it would be necessary to bind nearly one thousand 200 nm gold NPs to the cell surface to make a cell sufficiently heavier than the intrinsic mass variation of the cell population. The nearly 1,000 NPs bound to the cell surface would represent a nearly 10% coverage of the cell surface and would likely not be feasible. However, an important property of the suspended microchannel resonator is that it measures how much cells weigh relative to the mass density of the surrounding liquid solution. Thus, if blood cells, for example, were immersed in buffer with a mass density of approximately 1.07 g/cm$^3$, lymphocytes having such a density would be neutrally buoyant and would not be detected by the SMR. As a result the mean and width of a peak in the histogram would no longer relate to the number of NPs necessary for mass enhancement. In an ideal case in which density is perfectly matched, 5-10 NPs should be sufficient to allow detection. Because solution mass density is routinely adjusted over a wide range for separating blood cells, the inventors envision that the buffer conditions for making a particular cell type to be neutrally buoyant can be predetermined and then used routinely for CD4 counting assay.

Those of skill in the art will recognize that a goal in this aspect of the invention will be to determine the optimal solution mass density for which the SMR signal for unlabeled cells is minimized. As demonstrated by Boyum et al., both the osmolality and concentration of a nonionic species called Nycodenz can be used to tune a solution mass density with high precision. The amount of mass enhancement required for clear identification of target cells will depend on how well the solution mass density can be matched to the cell mass density as well as upon the amount of intrinsic variation in cell mass density. However, if there are 10-100 NPs bound to the target cells, their mass will increase by 0.1-1 pg if 100 nm NPs are used and by 1-10 pg if 200 nm NPs are used. It is recommended that the optimal NP size for enhancing signal relative to background while minimizing variability be determined. A scanning electron microscope can be used to visualize the NP labeling and then to validate findings.

It is not anticipated that signals from other cell types will interfere with counting of the target cells since each cell type has a different mass density. For example, if the solution density is perfectly matched to lymphocytes in a histogram peak, neutrophils in another peak will be centered near 7 pg on a histogram. Such a peak should be clearly distinguishable from a target cell peak. However, if needed, a differential measurement can be made wherein the histogram from an unlabeled sample is subtracted from a labeled one.

FIG. 6 provides an illustration of how solution mass density relates to the mass histogram as measured by the SMR. The effective mass measured by the SMR is proportional to the differential mass density between a cell and the surrounding solution. In FIG. 6a lymphocytes and neutrophils flow in the SMR in a buffer having a mass density of 1 g/cm$^3$ and the resulting histogram contains two peaks. Note that neutrophils are denser and larger than lymphocytes. In FIG. 6b the mass density of the surrounding solution of 1.07 g/cm$^3$ is perfectly matched to that of the lymphocytes. The lymphocytes are now effectively massless within the SMR and the resulting histogram contains only one peak resulting from the neutrophils. When the sample is mixed with NPs functionalized for CD4 lymphocytes, a second peak (not shown) will emerge with an average mass that is determined by the number of bound NPs. It should thus be possible to control the average mass of this peak by adjusting the INT size. We note that gold NPs are 20 times denser than solution.

Figure 7:
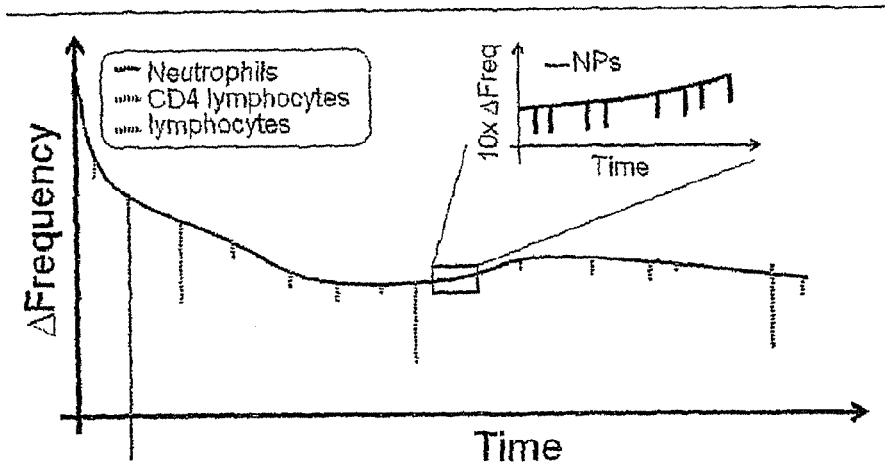
FIG. 7 is a graph of change in frequency vs. time.

Two general concerns about biosensors are signal degradation from bio-fouling and drift from temperature fluctuations of the environment. The former is particularly valid when the sample is derived from whole blood and the latter when the biosensor is operated in uncontrolled environments that exist outside of a centralized lab. However, the inventors believe that neither of these concerns will apply to the mass density matching technique discussed above. First of all, the mass density matching method is entirely flow-through and does not rely on detection at the microchannel surface. Second, the time response of the SMR signal from cells and NPs that flow through the microchannel is approximately 100 ms. While it is inevitable that biomaterial will bind to the surface and increase the microchannel mass (thereby lowering its resonant frequency), the time scale for such binding should be significantly longer than 100 ms. This effect should be true for temperature fluctuations that alter the resonant frequency. As a result, the slow time scale frequency drift resulting from temperature fluctuations and non-specific binding should not interfere with the ability to measure the height of 100 ms peaks from NPs and cells. This concept is shown schematically in FIG. 7. The frequency response of SMR as a mixture flows through a suspended microchannel resonator is shown in this figure. Although non-specific binding on the microchannels alters the frequency as well as temperature variations in the environment, the time scale of the resulting drift is much longer than the 100 ms pulse width. Ideally, the mass density of the solution is matched to the cell density. However, here we assume that the matching is not perfect and unlabeled lymphocytes are detected, but are small compared to mass enhanced lymphocytes. Neutrophils are denser than the solution and will create relatively large peaks. The inset in FIG. 7 shows the magnified response from single NPs that will be used to calibrate flow rate.

The protocol for obtaining a CD4 count by the mass-based approach is as follows:

(1) Mix whole blood with chemical lysate buffer for removing red blood cells and create three samples of the resulting mixture.

(2) Mix sample with predetermined amounts of NaCl and Nycodenz to make either lymphocytes or monocytes have neutral buoyancy.

(3) Mix one of the samples with gold NPs conjugated with antibodies for CD4+ cells (T lymphocytes+monocytes).

(4) Mix a second sample with gold NPs conjugated with CD14 antibodies for monocytes.

(5) Obtain a mass histogram for samples 1 and 2 and for a control sample 3.

(6) Subtract the control histogram from the histogram obtained from samples 1 and 2.

(7) Determine CD4 count by subtracting count of mass enhanced cells of the second sample from that of the first sample.

After the assay is completed, the SMR device may be cleaned and reused. Gold NPs may be purchased commercially with streptavidin functionalization. Antibodies may be biotinylated and attached to the functionalized NPs.

A suspended microchannel resonator requires approximately 100 ms to measure mass with a precision of approximately 5 fg and, because feedback is used to self-oscillate the cantilever, the dynamic range is infinite for all practical purposes. When counting mass enhanced CD4 cells as described above, the required precision should be considerably less. However, to make a conservative estimate of throughput, we will assume that 100 ms is required per cell. Our existing devices that were used to weigh $E.$ $coli$ have a volume of 10 pL (channel cross section of 3 by 8 μm$^2$) that yields a flow rate of 100 pL/sec for a 100 ms transit time. Devices for CD4 counting should have a cross section that is approximately an order of magnitude larger. Thus, a flow rate of 1 nL/sec can be achieved while preserving the 100 ms cell transit time. For a given patient, CD 4 cells are typically present at a concentration of approximately 100 cell/μl and there are 3,000-9,000 background white blood cells. For successful diagnosis, the detector should be capable of counting CD4 concentrations as low as 10 cells/μl. Assuming the lowest concentration of 10 cells/and that approximately 100 CD4 cells must be counted in order to obtain an accurate count, a single SMR will require 10$^4$ seconds or about 167 minutes.

The inventors believe that 167 minutes is a worst case scenario and that it should be possible to identify the mass-labeled cells from the background cells by reducing the average time to well below 100 ms since 5 fg precision will likely not be needed. Relaxing the precision will enable the flow rate to be increased. Furthermore, for some cases, a sufficiently accurate diagnostic may be obtained by counting fewer than 100 cells. A particularly attractive benefit of the matched mass density approach is that the flow rate can be continually calibrated during the CD4 measurement by counting the number of unbound NPs that pass through the SMR per unit time. Since the NP concentration will be sufficiently greater than the CD4 cell concentration, an NP is expected to flow through the channel every 1-10 seconds. Self-calibration avoids the need to use a different platform to measure flow rate or the need to use additional reagents to determine the volume consumed during the CD4 count. For SMR arrays, each channel will be calibrated simultaneously during the CD4 count. However, one potential source of error is that since the size difference between 100 nm NPs and lymphocytes is substantial, it is possible that the probability that a lymphocyte enters the suspended channel is different from that of the NP. We note that since the NP concentration is much greater than the cell concentration, it is possible for unbound NPs to occasionally flow through the SMR at the same time as the cells. However, since a single NP is 1-2 orders of magnitude lighter than a mass enhanced cell (assuming at least 10-100 NPs are bound), the aberrations from the unbound NPs should not alter the overall cell count.

Figure 8:
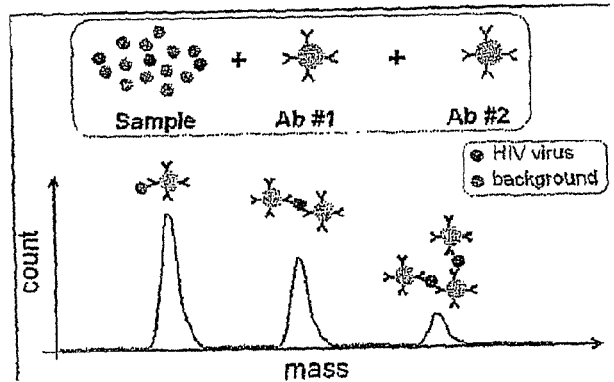
FIG. 8 is a graph of cell count vs. mass for HIV virus.

HIV viral load may be measured by an approach that is similar to that described above for counting CD4 cells. As shown in FIG. 8, the approach is based on using two different antibody-conjugated gold nanoparticles that are designed to recognize the virus at two different sites. The approach resembles a sandwich assay in which two NPs are brought together to form a dimer. Depending on the virus concentration relative to the NP concentration, structures containing more than two NPs can also be created. As a sample flows through the SMR, the resulting histogram reveals a series of peaks that correspond to NP monomers, dimers, trimers, etc. Based on previous measurements, the inventors have determined that the peak width from counting 100 nm NPs should enable dimers to be distinguished from monomers. Thus, an accurate viral count can then be obtained by summing the peak heights $0*peak\ 1+1*peak2+2*peak\ 3^+\ldots$.

A variation of this approach for detecting molecules and viruses has been previously demonstrated using two-color fluorescence coincidence by Agrawai et al. In their approach, two NPs of the dimer are color-coded quantum dots that emit green and red fluorescent light simultaneously when illuminated by a single laser excitation source. Based on quantitative studies, the authors found that the counting results are remarkably precise when the total numbers of counted molecules are more than 10. However, the complexity of their optical readout system is similar to that used for conventional flow cytometry. We anticipate that the mass readout with SMR will be of similar precision, but without the readout complexity.

To measure HIV viral load, CD44 and CD28 antibodies will be conjugated to gold NPs in separate containers. Various NP concentrations will be mixed with viral samples and dried on a smooth substrate. Similar to the CD4 cell count assay, the scanning electron microscope will be used to examine the resulting structures and to determine the optimal NP concentration. The assay will then be validated and optimized with the SMR.

A specific protocol for obtaining viral load with the SMR as shown in FIG. 8 is as follows:

(1) Starting sample will be serum rather than whole blood in order to eliminate cells.

(2) The sample is mixed with CD44 and CD28 NPs. NP concentration will be 10-100 larger than virus threshold concentration (approximately 10 virus/μl) to ensure that the two distinct binding sites on the virus are occupied.

(3) Obtain the mass histogram with the SMR.

In addition to distinguishing a population of cells, mass cytometry methods can be used to measure the absolute mass of cells and other targets. Such measurements are useful when cell mass correlates with disease or other physiological states. For example, the volume of red blood cells changes with state and it is likely that their total mass also changes. Measuring absolute mass requires calibration of the mass cytometer. In one method for calibration, particles of known mass are seeded into a sample containing red blood cells. The calibration particles create peaks in the mass cytometer signal whose magnitude can be related to the known mass of the calibration particles. The absolute masses of target cells can then be determined by relating their mass peaks to the calibration particle peaks. In the simplest case, the calibration particle mass will differ from the mass of the target cells so that the calibration and cell/target signals can be easily distinguished.

As a practical matter, the calibration particles will not have perfectly uniform mass, but rather some narrow distribution. The mass cytometer can still be calibrated to high precision so long as the mean mass is known accurately for the calibration particles, and enough peaks are measured during calibration to allow a precise measurement of the average calibration peak. An alternative method does not require seeding the sample with calibration particles, but instead performs the calibration and sample measurement steps sequentially. Absolute mass calibration can still be attained so long as the fluid densities are the same in the two cases, or the relative fluid densities are known. It is to be understood that a variety of calibration particles may be used, including, but not limited to, gold nanoparticles and polystyrene beads. In addition to measuring cell mass, this general method will have wide application in the mass measurement of other targets including, but not limited to, nanoparticles, micron-scale and sub-micron-scale beads, colloids, and any other particles that may be carried by a fluid medium.

Because of the high cost of equipment and reagents, sophisticated and delicate technology, and the need for complex maintenance and qualified personnel, the applicability of flow cytometry is limited in areas of the world with insufficient health infrastructure. See, Karcher et al., "Comparison of two alternative methods for CD4+ T-cell determination (Coulter Manual CD4 Count and CyFlow) against standard dual platform flow cytometry in Uganda," *Cytometry,* 70B 163 (2006).

As alluded to above, CD4+ cell counting approaches have been evaluated and compared to gold-standard FCM. In a first approach known as Cytospheres (Beckman Coulter), monoclonal antibody-coded latex spheres bind to cell expressing CD4 surface antigen. After lysis of erythrocytes, cells containing three or more spheres are counted with a light microscope. This approach is similar to the methodology discussed above in conjunction with FIG. 1 except that latex beads are used in place of nanoparticles and the labeled cells are counted optically. In a second approach, an automated two parameter FCM (CyFlow from Partek) is used in the volumetric protocol to count CD4+ cells that are marked with a single monoclonal fluorochrome-conjugated antibody in a known volume of blood. The erythrocyte lysing procedure is not required.

While both methods meet the performance metrics for reliable CD4+ counting, they do have relative strengths and weaknesses. Such merits are summarized by Karcher et al. The cytosphere method requires only an optical microscope, is robust and easy to handle under field conditions, and requires minimal maintenance and training. However, the number of samples that can be analyzed per day is relatively low (about 2-4/hr) due to the time consuming counting procedure. In addition, the fidelity depends on individual skills and experience of the laboratory technician. Results are also less accurate due to the low number of cells counted (~250) per assay. Finally, the cost per assay (~$10) is relatively high due to the reagents. In contrast, the cost of the CyFlow is $25,000 and the cost per assay of ~$2 is relatively low. The CyFlow can analyze about ten samples per hour, but it requires more technical expertise and maintenance is more complicated. Repair procedures usually require an outside specialist and experience with the technique under field conditions is scarce. However, the CyFlow results are more reliable than the Cytosphere method.

Other applications for flow cytometry that would be appropriate for mass based flow cytometry include the analysis of bacteria, spores and viruses. For example, Yamaguchi et al. in "Rapid detection of respiring Escherichia coli 0157:H7 in apple juice, milk, and ground beef by flow cytometry," Cytometry 54A 27 (2003) used the FCM for the rapid detection of E. coli O157:H7 in apple juice, milk, and ground beef. Stopa used the FCM technique to detect Bacillus anthracis spores. See, Stopa, "The flow cytometry of bacillus anthracis spores revisted," Cytometry 41 237 (2000). Steen, as well as Davey and Kell, provide a detailed review on detecting microbial populations with the FCM. Although viruses are not typical targets for conventional FCM, the mass labeling techniques and mass cytometry described in these embodiments could be employed for numerous applications in virology. Examples included measurement of viral load of HIV or hepatitis.

Figure 9:
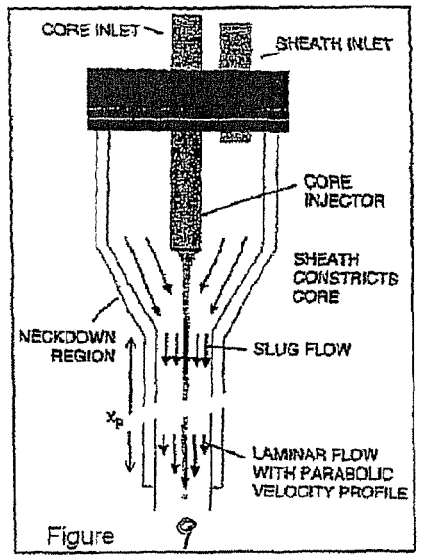
FIG. 9 is a cross-sectional view of a conventional flow cytometer in which sheath flow or hydrodynamic focusing is used to confine a sample or core fluid containing cells.

In a conventional FCM, sheath flow or hydrodynamic focusing is used to confine a sample or core fluid containing the cells. FIG. 9 shows such an approach. This arrangement improves the precision for positioning and aligning cells and also reduces the likelihood of obstruction of the flow system. The inventors herein envision that similar approaches can be used to provide controllable delivery of cells to a suspended microchannel resonator. However, once the cells enter the sensor, precision positioning is no longer required since the mass change is detected and independent of lateral position within the sensor.

Yet another embodiment of the invention is shown in FIG. 10. Nanoparticles conjugated to primary and secondary antibodies are mixed with targets that have multiple binding epitopes. If the target concentration is sufficiently lower than the nanoparticle conjugate concentration, the majority of the targets will bind to the primary and secondary antibodies to form dimers in which two nanoparticles are connected. The sample is then flowed through a suspended microchannel resonator and the mass of each component in the mixture is measured and the histogram is created. The dimers are counted and related to the initial target concentration.

Flow rate calibration alluded to above in conjunction with CD4 measurement is very general. It does not require density matching since gold is twenty times denser than water. For flow rate calibration, the number of unbound nanoparticles that pass through a resonator per unit time is monitored to provide flow rate calibration.

The contents of all the following references are incorporated herein by reference.

It is recognized that modifications and variations of the inventions disclosed herein will be apparent to those of skill in the art and it is intended that all such modifications and variations be included within the scope of the appended claims.

References

Gifford et al., "Parallel microchannel-based measurements of individual erythrocyte areas and volumes," Biophysical Journal, 84 623 (2003).

Brando et al., "Cytofluorometric methods for assessing absolute numbers of cell subsets in blood," Cytometry, 42 327 (2000).

Karcher et al., "Comparison of two alternative methods for CD4+ T-cell determination (Coulter Manual CD4 Count and CyFlow) against standard dual platform flow cytometry in Uganda," Cytometry, 70B 163 (2006)

Yamaguchi et al., "Rapid detection of respiring Escherichia coli 0157:H7 in apple juice, milk, ground beef by flow cytometry," Cytometry, 54A 27 (2003).

Stopa, "The flow cytometry of bacillus anthracis spores revisited," Cytometry 41 237 (2000).

Sklar, Flow cytometry for biotechnology, Oxford University Press (2005), article entitled "Elastomeric microfabricated fluorescence-activated cell sorters," by Fu, Yokobayashi, Arnold and Quake, p. 68.

Steen, "Flow cytometry of bacteria: glimpses from the past with a view to the future," Journal of Microbiological Methods 42 65 (2000).

David and Kell, "Flow cytometry and cell sorting of heterogeneous microbial populations" the importance of single-cell analyses," Microbiology Reviews 60 641 (1996).

T. P. Burg M. Godin, W. Shen, G. Carlson, J. S. Foster, K. Babcock, and S. R. Manalis. Weighing of Biomolecules, Single Cells, and Single Nanoparticles in Fluid. Nature 2007; 446 1066-1069

Herzenberg L A, Parks D, Sahaf B, Perez O, Roederer M, Herzenberg L A, "The history and future of the fluorescence activated cell sorter and flow cytometry: A view from Stanford," Clinical Chemistry, 48:10 1819-1827 (2002).

Shapiro H M, "The Evolution of Cytometers," Cytometry Part A 58A: 13-20 (2004).

Goodwin P M, Johnson M E, Martin J C, Ambrose W O, Marrone B L, Jett J H, Keller R A, "Rapid sizing of individual fluorescently stained DNA fragments by flow cytometry," Nucleic Acids Res 21:803-806 (1993).

Chou H P, Spence C, Scherer A, Quake S R, "A microfabricated device for sizing and sorting DNA molecules," Proc. Natl. Acad Sci, 96:11-13 (1999).

Strauss K, Hannet I, Engels S, et al. Performance evaluation of the FACSCount system: A dedicated system for clinical cellular analysis. Cytometry 1996; 26:52-59

Van Dilla M A, Fulwyler M J, Boone I U. Volume distribution and separation of normal leucocytes. Proc Soc Exp Biol Med 1967; 125:367-370.

Boyum A, Lovbaug D, Tresland L, and Nordlie E M, "Separation of leucocytes: improved cell purity by fine adjustments of gradient medium density and osmolality," Scand. J. Immunol. 34, 697-712 (1991).

What is claimed is:

1. A method for measuring absolute mass of targets comprising:
    seeding calibration particles of known mass into a sample containing targets of unknown mass;
    running the sample with calibration particles through a suspended microchannel resonator;
    measuring peaks in a mass histogram resulting from the measured discrete response of each of the calibration particles' known mass on the resonant behavior of the resonator;
    measuring peaks in the mass histogram resulting from the targets' mass has been inserted therefor on the resonant behavior of the resonator; and
    determining the mass of the targets by comparing and correlating the target mass peaks to the calibration particle peaks.

2. A flow rate calibration method comprising:
    providing a sample;
    adding nanoparticles to the sample;
    passing the sample through a suspended microchannel resonator;

monitoring the number of nanoparticles that pass through the resonator per unit time by measuring the discrete response of each of the nanoparticles' mass on the resonant behavior of the resonator; and determining the sample flow rate from the number of particles per unit time passing through the resonator.

\* \* \* \* \*